(12) United States Patent
Wisløff et al.

(10) Patent No.: US 10,973,421 B2
(45) Date of Patent: Apr. 13, 2021

(54) HEALTH RISK INDICATOR DETERMINATION

(71) Applicant: BEIJING SHUNYUAN KAIHUA TECHNOLOGY LIMITED, Beijing (CN)

(72) Inventors: Ulrik Wisløff, Jonsvatnet (NO); Christian Ragnar Gutvik, Trondheim (NO)

(73) Assignee: BEIJING SHUNYUAN KAIHUA TECHNOLOGY CO., LTD., Beijing (CN)

(*) Notice: Subject to any disclaimer, the term of this patent is extended or adjusted under 35 U.S.C. 154(b) by 432 days.

(21) Appl. No.: 14/565,860

(22) Filed: Dec. 10, 2014

(65) Prior Publication Data
US 2015/0265170 A1   Sep. 24, 2015

(30) Foreign Application Priority Data
Mar. 20, 2014   (EP) .................................... 14160936

(51) Int. Cl.
*A61B 5/024*   (2006.01)
*A61B 5/00*    (2006.01)
(Continued)

(52) U.S. Cl.
CPC ...... *A61B 5/02438* (2013.01); *A61B 5/02416* (2013.01); *A61B 5/7275* (2013.01);
(Continued)

(58) Field of Classification Search
None
See application file for complete search history.

(56) References Cited

U.S. PATENT DOCUMENTS

| 5,243,992 A * | 9/1993 | Eckerle ................ G04G 21/025 600/485 |
| 2002/0077536 A1* | 6/2002 | Diab .................. A61B 5/14546 600/323 |

(Continued)

FOREIGN PATENT DOCUMENTS

| EP | 2921105 B1 | 2/2018 |
| WO | WO-2009/074985 A2 | 6/2009 |
| WO | WO-2013/166341 A1 | 11/2013 |

OTHER PUBLICATIONS

Uth et al., Estimation of VO2max from the ratio between HRmax and HRrest—the Heart Rate Ratio Method,Eur J Appl Physiol (2004) 91: 111-115.*

(Continued)

*Primary Examiner* — Kaylee R Wilson
*Assistant Examiner* — Jay B Shah
(74) *Attorney, Agent, or Firm* — Young Basile Hanlon & MacFarlane, P.C.

(57) ABSTRACT

The present disclosure relates to the conversion of biometric data to meaningful heath risk indications. According to one aspect, there is provided a method of determining a health risk indicator for a user by: obtaining heart rate data for the user recorded over a monitoring period of at least one day; processing said heart rate data in dependence on biometric data for the user to determine an aggregate heartbeat value for the user over said monitoring period; and determining said health risk indicator in dependence on said aggregate heartbeat value.

17 Claims, 7 Drawing Sheets

(51) Int. Cl.
*G16H 50/30* (2018.01)
*A61B 5/0205* (2006.01)
*A61B 5/11* (2006.01)
*A61B 5/021* (2006.01)
*A61B 5/145* (2006.01)

(52) U.S. Cl.
CPC ............ *G16H 50/30* (2018.01); *A61B 5/0024* (2013.01); *A61B 5/021* (2013.01); *A61B 5/0205* (2013.01); *A61B 5/1118* (2013.01); *A61B 5/14532* (2013.01); *A61B 5/14542* (2013.01); *A61B 5/4866* (2013.01); *A61B 5/6824* (2013.01); *A61B 5/6828* (2013.01); *A61B 5/6898* (2013.01); *A61B 5/7203* (2013.01); *A61B 5/725* (2013.01); *A61B 2503/12* (2013.01); *A61B 2562/0219* (2013.01)

(56) References Cited

U.S. PATENT DOCUMENTS

| | | | | |
|---|---|---|---|---|
| 2007/0135264 | A1* | 6/2007 | Rosenberg | A63B 24/0062 482/8 |
| 2007/0208266 | A1* | 9/2007 | Hadley | A61B 5/02405 600/519 |
| 2010/0016678 | A1* | 1/2010 | Beck | A61B 5/0031 600/300 |
| 2010/0298899 | A1* | 11/2010 | Donnelly | A61B 5/02055 607/6 |
| 2012/0316456 | A1* | 12/2012 | Rahman | G06F 1/163 600/547 |
| 2014/0073486 | A1 | 3/2014 | Ahmed et al. | |

OTHER PUBLICATIONS

Kodama et al, Cardiorespiratory Fitness as a Quantitative Predictor of All-Cause Mortality and Cardiovascular Events in Healthy Men and Women. JAMA, May 20, 2009; vol. 301, No. 19.*

Nauman, Javaid et al., "Temporal Changes in Resting Heart Rate and Deaths From Ischemic Heart Disease," *JAMA*, 2011, 306(23):2579-2587.

Rennie, Kirsten et al., "Estimating energy expenditure by heart-rate monitoring without individual calibration," *Medicine & Science in Sports & Exercise*, 2001, p. 939-945.

Wareham, Nicholas J. et al., "A quantitative analysis of the relationship between habitual energy expenditure, fitness and the metabolic cardiovascular syndrome," *British Journal of Nutrition*, 1998, 80:235-241.

* cited by examiner

HEALTH RISK INDICATOR DETERMINATION

BACKGROUND

According to The World Health Organization (WHO), physical inactivity is the fourth major cause of premature death worldwide (WHO, 2009) and a recent series of publications shows that inactivity kills about 6 million people every year worldwide; a similar number as smoking (I-M Lee, The Lancet 2012). It is also well established that about 80% of all adults do not fulfil the criteria of current recommendations for physical activity (see e.g. Folkehelseinstiuttet 2009) and that major reductions in lifestyle related diseases have to come from population-wide, cost-effective interventions such as systematically increased physical activity level (United Nations General Assembly A/66/83, 2011).

The public is overwhelmed by exercise advice and frequent disputes as to how, how often and for how long we should exercise. Navigating this information, which covers the whole range from professional athletes to heart patients, can prove confusing and frustrating. This in itself can lead to a lack of motivation.

Fitness monitoring devices such as pedometers are available. However, many fitness monitoring devices are based on motion sensing alone, which can lead to inaccurate estimation of activity levels. For example a wrist-worn accelerometer could indicate a higher activity level for a period during which a user is eating than a period during which they are climbing stairs.

While some fitness monitoring devices are based on personal heart rate monitors these tend to be aimed at fitness enthusiasts wishing to track their training. They do not provide meaningful health risk indications suitable for those who only wish to reduce their risk of developing lifestyle-related (e.g. cardiovascular) diseases. Prevention of disease is a common motivation for exercising. For older people in particular it is often the primary motivation.

There is a need for an accurate, yet simple and unified, recommendation about activity level, which directly links to an individuals' health.

SUMMARY

The present disclosure relates to the conversion of biometric data to meaningful heath risk indications. More specifically, aspects of the disclosure relate to a method and system for determining a health risk indicator for a user from heart rate data.

According to a first aspect, there is provided a method of determining a health risk indicator for a user by: obtaining heart rate data for the user recorded over a monitoring period of at least one day; processing said heart rate data in dependence on biometric data for the user to determine an aggregate heartbeat value for the user over said monitoring period; and determining said health risk indicator in dependence on said aggregate heartbeat value.

Said biometric data could comprise a resting heart rate value for the user and a maximum heart rate value for the user.

The health risk indicator could be provided to the user.

The monitoring period could be at least two days. The monitoring period could be at least three days. The monitoring period could be at least five days. The monitoring period could be one week. The monitoring period could be a fortnight. The monitoring period could be one month. The monitoring period could be configurable by the user and/or a health professional.

The method could further comprise sensing the user's pulse over the monitoring period to produce a series of pulse measurements and determining the aggregate heartbeat value from said series of pulse measurements.

The series of pulse measurements could be extrapolated to produce an evenly distributed series of data points or a continuous heart rate function over the monitoring period.

Said processing could further comprise normalising the heart rate data, an evenly distributed series of data points derived from the heart rate data or a continuous function derived from the heart rate data by subtracting said resting heart rate value and dividing the result by the difference between said maximum heart rate value and the resting heart rate value. Such processing could be to calculate an intensity value.

The aggregate heartbeat value might not be a pure sum of heartbeats; the aggregate heartbeat value weighting heart rate values such that the higher the heart rate value, the more weight it is given. Intensity values could also be weighted in this manner to provide intensity scores.

Said intensity scores could be calculated as exponential powers of the intensity values.

The aggregate heartbeat value could be determined by summing intensity scores derived from the heart rate data over the monitoring period.

An activity score could be determined by summing discrete intensity scores or integrating a continuous function derived from the heart rate data over the monitoring period.

The health risk indicator could be determined by statistical fitting of the aggregate heartbeat value with population survey data.

The sensing could be periodic. A sampling rate of said periodic sensing could be variable over time. Said sampling rate could be increased in response to a determination that the user's heart rate has increased above a first predetermined threshold value; and/or said sampling rate could be decreased in response to a determination that the user's heart rate has decreased below a second predetermined threshold value.

The method could further comprise obtaining data indicating movement of the user over the monitoring period; and reducing the weighting applied to heart rate values determined to be greater than a predetermined threshold higher than predetermined expected heart rate values associated with the data indicating movement of the user for the time those heart rate values correspond to.

The method could be repeated periodically. A repetition period could be equal to the monitoring period such that the method is repeated consecutively. Alternatively, a repetition period could be less than the monitoring period such that the method is performed in a sliding window.

The health risk indicator could comprise an indication of whether or not the user is classed as being physically active enough in order to substantially reduce the risk of developing one or more lifestyle-related diseases.

The method could further comprise estimating the user's peak aerobic capacity using a first order low pass filter on the aggregate heartbeat value or a value derived therefrom and biometric data for the user. Said biometric data could comprise one or more of resting heart rate, age and body mass index.

According to a second aspect, there is provided a computer program product comprising computer-executable instructions for performing the method of the first aspect.

According to a third aspect, there is provided a system for determining a health risk indicator for a user, said system comprising: a data input configured to receive heart rate data for the user over a monitoring period of at least one day; and a processor configured to: process said heart rate data in dependence on biometric data for the user to determine an aggregate heartbeat value for the user over said monitoring period; and determine said health risk indicator in dependence on said aggregate heartbeat value.

Said biometric data could comprise a resting heart rate value for the user and a maximum heart rate value for the user.

Said system could comprise a user interface configured to provide the health risk indicator to the user.

The system could further comprise: a sensor configured to sense the user's pulse over said monitoring period to produce a series of pulse measurements; and a processor configured to determine the heart rate data from said series of pulse measurements.

According to a fourth aspect, there is provided a method of determining a health risk indicator for a user by: receiving a series of heart rate measurements taken from the user over a monitoring period of at least five days at intervals of no more than fifteen minutes; processing each of said measurements using the user's rest and maximum heart rates to produce a series of normalised heart rate values; weighting each normalised heart rate value to produce a series of weighted heart rate values; aggregating said weighted heart rate values over said monitoring period to produce a heartbeat aggregate; and determining said health risk indicator by statistical fitting of said heartbeat aggregate with population study data. The health risk indicator can then be provided to the user. The user's pulse can be sensed over the monitoring period to produce the series of heart rate measurements.

According to a fifth aspect, there is provided a system for determining a health risk indicator, said system comprising: a data input configured to receive a series of heart rate measurements taken from a user over a monitoring period of at least five days at intervals of no more than fifteen minutes; and a processor configured to: process each of said measurements using the user's rest and maximum heart rates to produce a series of normalised heart rate values; weight each normalised heart rate value to produce a series of weighted heart rate values; aggregate said weighted heart rate values over said monitoring period to produce a heartbeat aggregate; and determine said health risk indicator by statistical fitting of said heartbeat aggregate with population study data. A user interface can be configured to provide the health risk indicator to the user. A sensor can be configured to sense the user's pulse over said monitoring period to produce the series of heart rate measurements.

BRIEF DESCRIPTION OF THE FIGURES

Aspects of the present disclosure will now be described by way of example with reference to the accompanying figures. In the figures.

DETAILED DESCRIPTION

The following description is presented to enable any person skilled in the art to make and use the system, and is provided in the context of a particular application. Various modifications to the disclosed examples will be readily apparent to those skilled in the art.

The general principles defined herein can be applied to other embodiments and applications without departing from the spirit and scope of the present disclosure. Thus, the present invention is not intended to be limited to the embodiments shown, but is to be accorded the widest scope consistent with the principles and features disclosed herein.

Recent (as yet unpublished) research has shown that accumulated number of heartbeats over time is the most important predictor for general cardiovascular health status. Presented below is a method for converting heart rate data to a health risk indicator and possible implementations of systems for collecting and processing heart rate data and informing a user of a health risk indicator derived therefrom.

Monitoring heart rate provides a more accurate way to track activity level for the purpose of improving health than, for example, number of steps taken. The former rates walking uphill higher than walking the same number of steps on a flat surface, whereas the latter will rate these activities as the same (or even lower during uphill walking for some gaits) despite the significant difference in physical exertion required. Further, an aggregate heartbeat based system will rate a long hike in the mountains equally with high intensity interval training, if both activities promote the same aggregate heartbeat value, making a system based on aggregate heartbeat measurement suitable for use for health improvement across the population regardless of age or physical capability.

Figure 1:
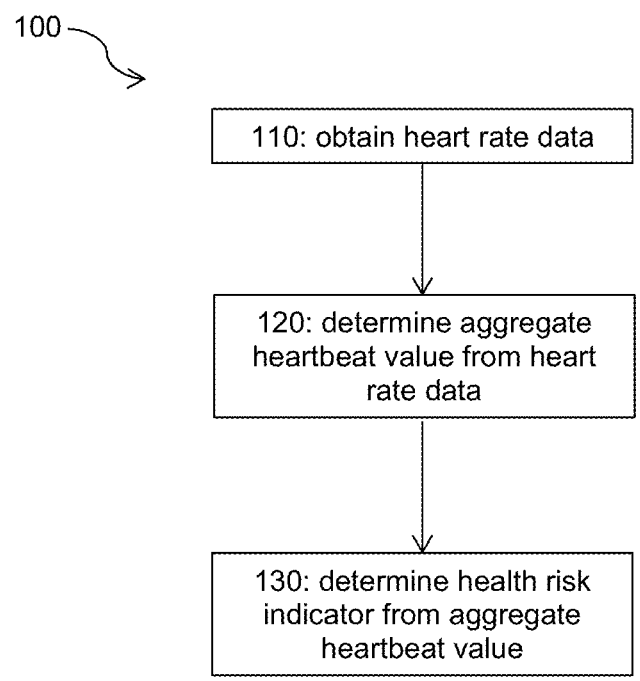
FIG. 1 sets out a general method.

FIG. 1 is a flowchart of a general method 100 for determining a health risk indicator for a user from heart rate data collected from them. At step 110, heart rate data for the user recorded over a monitoring period of at least five days, for example 1 week, is obtained. At step 120, that heart rate data is processed in dependence on a resting heart rate value for the user and a maximum heart rate value for the user to determine an aggregate heartbeat value for the user over the monitoring period. At step 130, a health risk indicator is determined in dependence on the aggregate heartbeat value.

Figure 2:
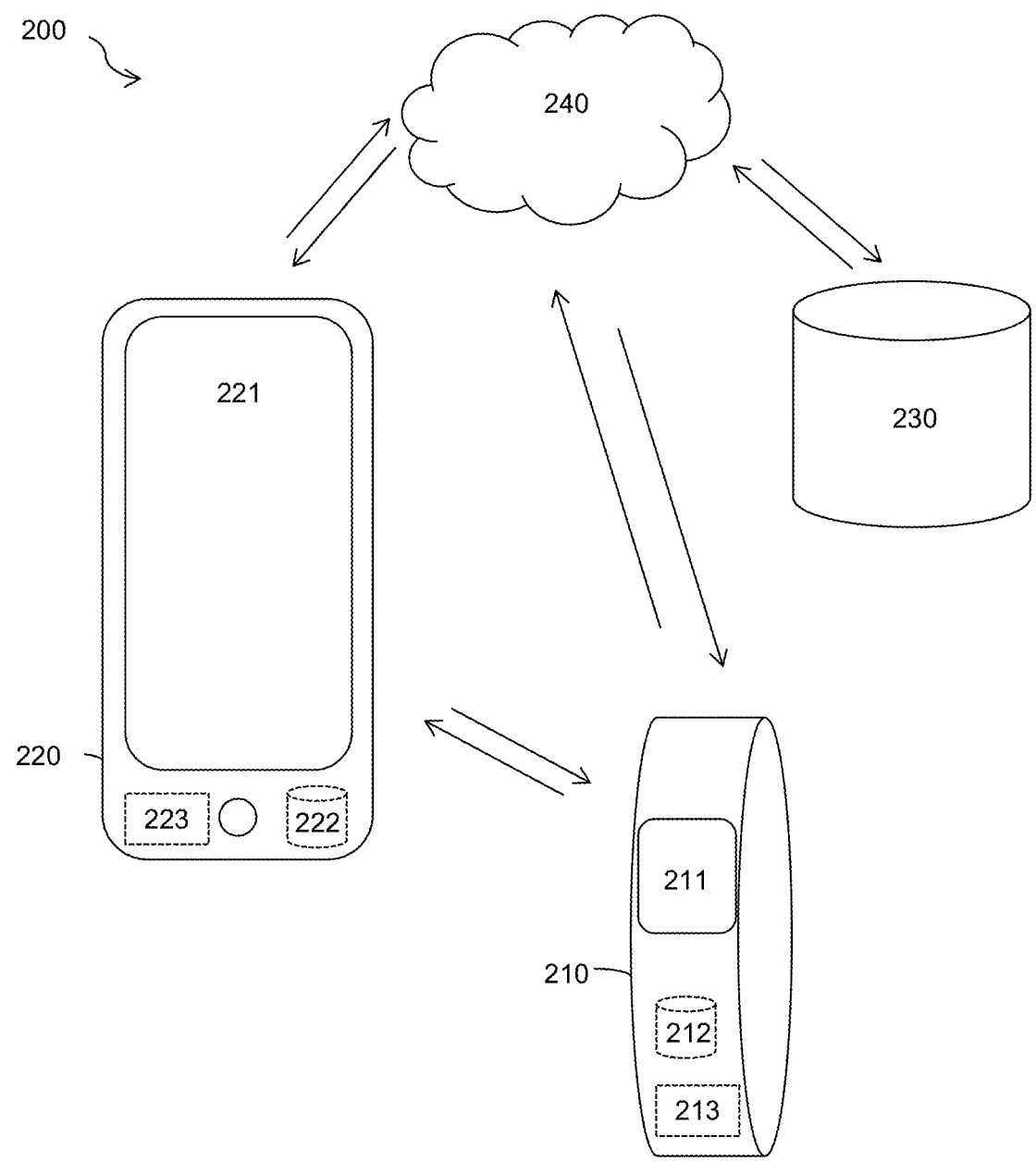
FIG. 2 illustrates an example system.

FIG. 2 is a schematic of an example system for providing a user with a health risk indicator.

Biometric data including at least heart rate data is collected from a user by one or more sensors comprised in a sensor device 210. Sensor device 210 could be a wearable device, for example a sensor wristband or chest strap. Heart rate data could be collected by, for example, a photoplethysmography (PPG) sensor. Other kinds of sensors could also be provided, for example an accelerometer (motion sensor), blood pressure sensor, glucose sensor, blood gas sensor, pressure sensor or any other sensors which could be used to measure user activity, physiological or environmental parameters. Data obtained from such sensors could be taken into account in determining health risk indicators and/or could be part of a wider health/fitness monitoring suite enabling a user or healthcare professional to obtain more detailed health indication information if required.

The user's resting and maximum heart rates are also obtained. Resting heart rate can be obtained by determining the lowest heart rate value measured by sensor device 210 over the monitoring period. Alternatively, resting heart rate could be measured by the user or a healthcare professional by any known method and manually input to the system via a user interface. Maximum heart rate can be obtained by determining the highest heart rate value measured by sensor device 210 over the monitoring period. Alternatively maximum heart rate could be measured by the user or a healthcare professional by any known method and manually input to the system via a user interface.

The sensor device 210 could comprise a user interface 211 and/or could comprise means for transferring data to a user device 220 having a user interface 221 such as a mobile phone (e.g. a smartphone), tablet, laptop or personal computer. Such data transfer means could comprise a wired connection such as a Universal Serial Bus (USB) line or a wireless link such as a Wi-Fi or Bluetooth™ connection between a transmitter and associated antenna comprised in the sensor device 210 and a receiver and associated antenna comprised in the user device 220. The sensor device 210 and/or the user device 220 could each run software suitable for implementing part or all of the method described herein by means of memories 212 and 222 and processors 213 and 223 respectively. For example the user device 220 could run a dedicated application or could run a general-purpose web browser through which a web-based application could be accessed. Suitable user interfaces include at least touchscreens, keyboards and/or touchpads or mice or microphones with associated voice recognition capabilities.

The system could have a calibration mode to collect resting and maximum heart rate from the user without requiring the assistance of a healthcare professional. For example software run on the sensor device 210 or user device 220 could cause a user interface of one of those devices to prompt a user to perform a calibration on first switching on sensor device 210 or opening an associated application with user device 220. The user could also be presented with an option to skip the calibration at that point but, if they select the skip option, they could be prompted to perform the calibration at the end of the monitoring period.

When the user selects calibration mode, they can be instructed by a user interface to get into a comfortable position for measuring resting heart rate and start a timer when ready. While the timer is running they could be instructed not to perform any physical activity until the timer, which can for example be displayed on a visual user interface of the device, expires. The timer could for example be for one minute. Towards the end of the timer period the sensor device 210 could take a heart rate reading and record this as the user's resting heart rate. Alternatively, sensor device 210 could monitor the user's heart rate over some or all of the timer period, for example at 5 second intervals, and select the lowest measured rate to record as the user's resting heart rate. Once the user's resting heart rate has been obtained, the user could be prompted to get on to some gym equipment (e.g. a treadmill, cross-trainer, rowing machine or exercise bike), or find somewhere to run, cycle or similar and start another timer when ready. While the timer is running they could be instructed to exercise at maximum exertion (e.g. run as fast as possible). The timer could for example be for 5 minutes. Sensor device 210 could monitor the user's heart rate over some or all of the timer period and select the highest measured rate to record as the user's maximum heart rate.

During the monitoring period itself, sensor device 210 can monitor the user's heart rate continuously or sample at intervals. If sensor device 210 is battery powered, the monitoring could be arranged such that a fully charged battery will outlast the monitoring period. Interval sampling could be periodic. A typical sampling rate could be once per minute. A minimum sampling rate could be once every 15 minutes.

The sensor device 210 could store the heart rate data in local memory 212. Alternatively or additionally the sensor device 210 could be provided with data transfer means such as those described above to convey the heart rate data to a user device 220 for storing in its local memory 222 or upload it directly to a network 240 such as the internet for transmission to a server 230.

The heart rate data can be processed by an internal processor 213 of the sensor device 210, a processor 223 of the user device 220, at the server 230 or by any combination of these performing any suitable combination of the processing steps.

Sampling rate could be variable. This can help to achieve a suitable balance between data accuracy and (battery) power consumption. For example if heart rate is determined to have risen above a first predetermined threshold value (indicating that physical activity is being undertaken), for example 60% of the user's maximum heart rate relative to their resting heart rate, the sampling rate could be increased, for example to once every 15 seconds. The sampling rate could be returned to its standard value when the user's heart rate is determined to have fallen below the first threshold, or to have stayed below the first threshold for a predetermined period, for example 5 minutes. Similarly, if the user's heart rate is determined to have fallen below a second predetermined threshold value, for example 5% of the user's maximum heart rate relative to their resting heart rate, or to have stayed below such a threshold for a predetermined period, for example 10 minutes (indicating that the user is sleeping), the sampling rate could be decreased, for example to once every 10 minutes. The sampling rate could be returned to its standard value when the user's heart rate is determined to have exceeded the second threshold again.

Figure 3:
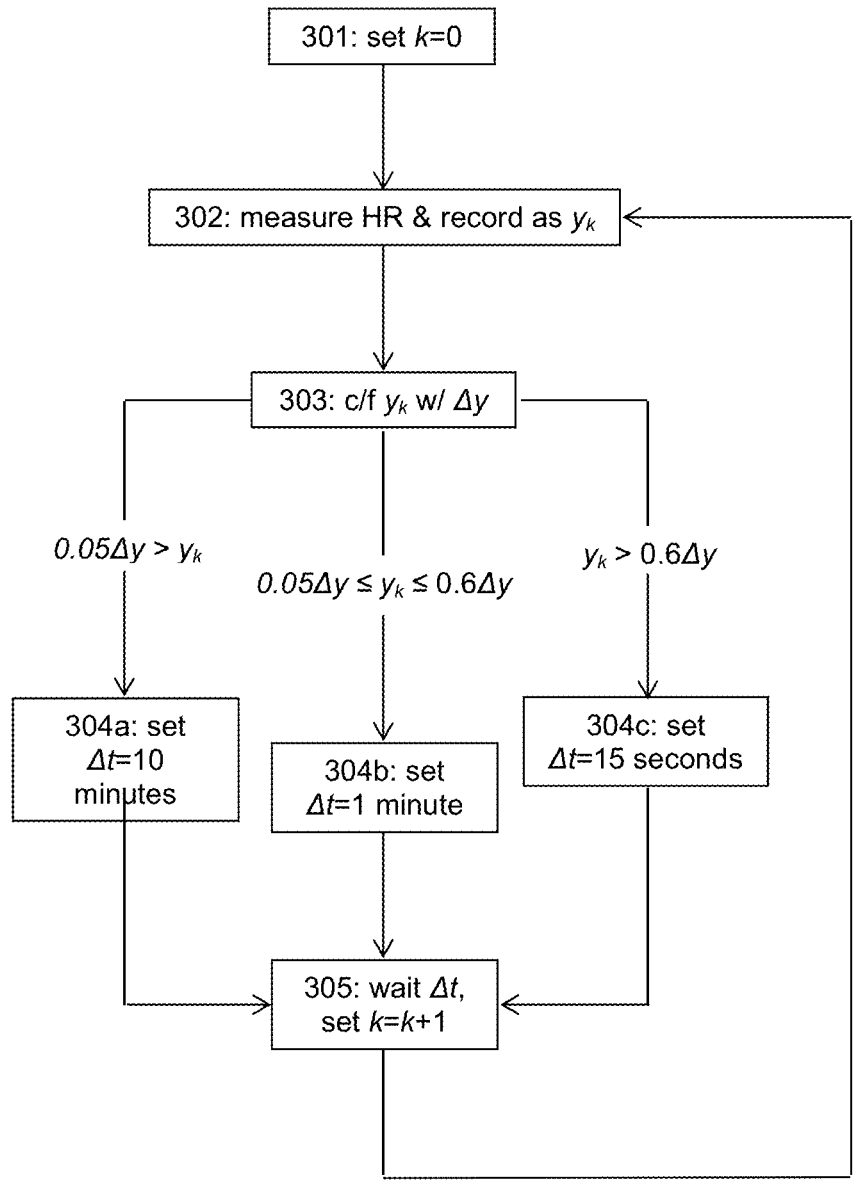
FIG. 3 sets out an example sample rate variation scheme.

FIG. 3 is a flowchart showing an example scheme for varying sampling rate. At 301, a sample counter k is set to zero. At 302, the user's current heart rate is measured and recorded as $y_k$. At 303, $y_k$ is compared to $\Delta y$, the heat rate range of the user where:

$$\Delta y = y_{max} - y_{rest} \quad (1)$$

i.e. the difference between the user's resting and maximum heart rates as previously recorded. If the current heart rate value is less than 5% of $\Delta y$, then a sampling interval $\Delta t$ is set to 10 minutes at 304a. If the current heart rate value is between 5% and 60% of $\Delta y$, then $\Delta t$ is set to 1 minute at 304b. If the current heart rate value is greater than 60% of $\Delta y$, then $\Delta t$ is set to 15 seconds at 304c. At 305, a timer is set to wait for $\Delta t$, and when it has expired the value of k is incremented by 1 and the process returns to 302.

Figure 4:
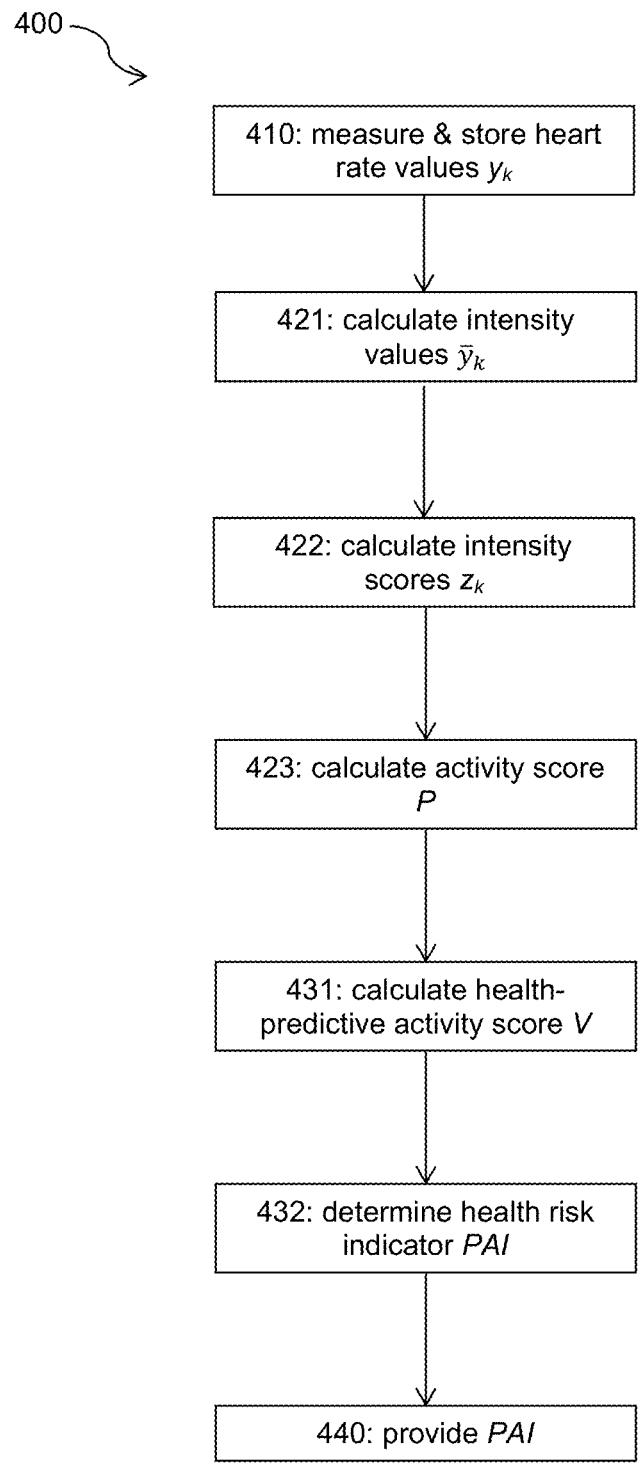
FIG. 4 sets out an example method.

An example processing method 400 is set out in FIG. 4.

At step 410, a series of heart rate values $y_k$ are measured and stored. This series of instantaneous sampled heart rate values is recorded over the monitoring period defined as time, t=−T to t=0. Optionally, a continuous heart rate function y(t) could be extrapolated from the series of heart rate values.

At step 421, the heart rate values (or heart rate function) are (is) converted to a series of intensity values $\bar{y}_k$ (or an intensity value function $\bar{y}(t)$). This could be done using a linear intensity scaling. In this example method, intensity conversion is a normalisation with respect to the user's heart rate range (from resting heart rate $y_{rest}$ to maximum heart rate $y_{max}$). This produces a series of normalised heart rate values $\bar{y}_k$ (or a continuous normalised heart rate function $\bar{y}(t)$) according to equations 2. This gives an indication of instantaneous exertion over the monitoring period.

$$\bar{y}_k = \frac{y_k - y_{rest}}{\Delta y}; \; \bar{y}(t) = \frac{y(t) - y_{rest}}{\Delta y} \quad (2)$$

Alternative intensity scaling could be used, for example by calculating a percentage of individual fitness level based on peak oxygen uptake.

If a variable sampling rate was used to record the heart rate data then inter-sample data points can optionally be extrapolated between samples for periods when the sampling rate was at less than its maximum value to produce a series of data points at constant intervals. For example linear interpolation between the two (temporally) nearest sampled heart rate values to each desired extrapolated data point could be used. This extrapolation can be performed before or after intensity scaling. Alternatively, if no extrapolation of inter-sample data points is performed, then variable sampling rates as described above, with higher sampling rates used during periods of greater exertion, would result in higher weighting of heartbeats during exercise on calculation of activity score as described below.

At step 422, the intensity values (or intensity value function) are (is) converted to a series of intensity scores $z_k$ (or an intensity score function $z(t)$). This could be done using a power function. In this example method, intensity score calculation is done using an exponential function according to equations 3:

$$z_k = c_1(e^{c_2 \bar{y}_k} - 1); z(t) = c_1(e^{c_2 \bar{y}(t)} - 1) \quad (3)$$

where $c_1$ is a constant scaling factor (which can be unity) and $c_2$ is a constant weighting factor. Alternative power functions or other scaling functions could be used, for example quadratic or cubic.

The activity score, P, is then computed at step 423. The activity score is a heartbeat aggregate over the monitoring period, T, for example the Euler integration sum (or definite integral) of the intensity scores (or intensity function) over the monitoring period as per equations 4.

$$P = \Sigma_{i=-N}^{k} \Delta t_i z_i; P = \int_{-T}^{0} z(t) dt \quad (4)$$

where N is the total number of sample points over the monitoring period and $\Delta t$ is the sampling interval.

At step 431, a health-predictive activity score, V, is determined as an explicit function of activity score P, for example according to equation 5:

$$V = c_3 + c_4(1 - e^{-P}) \quad (5)$$

where $c_3$ and $c_4$ are constants determined from population study data. For model calibration the health-predictive activity score can be statistically linked to peak oxygen uptake of population study subjects since peak oxygen uptake is a good predictor of cardiovascular health. (Peak oxygen uptake of the user need not necessarily be known, but the health-predictive activity score can be compared with the activity score needed to achieve a certain peak oxygen uptake over time to determine a health risk indicator.)

Any or all of constants $c_1$ to $c_4$ could be chosen from a plurality of options according to one or more user characteristics such as gender, age, weight, height etc. For example, suitable constants for a male user could be $c_1 = 4.51$, $c_2 = 7.73$, $c_3 = 29.5$, $c_4 = 19.8$.

One or more health risk indicators can be derived from the health-predictive activity score at step 432. For example, a health risk indicator could be a linear scaling of the health-predictive activity score, where complete inactivity gives the value 0 and the value 100 indicates minimal risk of developing lifestyle-related diseases. The health risk indicator could be expressed relative to a threshold for reduced/increased risk to health. For example, a health risk indicator of greater than 45 for men, or 35 for women, could indicate reduced risk, while a health risk indicator below that threshold could indicate increased risk.

A health risk indicator could be expressed as a personal activity index, PAI, as defined in equation 6:

$$PAI = \frac{100(V - c_3)}{V_{threshold} - c_3} \quad (6)$$

where $V_{threshold}$ is a constant which could optionally be chosen from a plurality of options according to one or more user characteristics such as gender, age, weight, height etc. It could for example be 45 for a male user or 35 for a female user.

A health risk indicator could be a binary indication of whether or not the user has been physically active enough over the monitoring period to improve their activity score compared to a previous monitoring period. Alternatively, it could be a binary indication of whether or not the user has been active enough over the monitoring period to reduce their general risk of developing lifestyle-related diseases compared to a previous monitoring period. If a greater level of detail is desired, one or more binary health risk indicators could be provided to indicate whether or not the user has been active enough over the monitoring period to reduce their risk of developing a corresponding one or more specific lifestyle-related diseases/conditions compared to a previous monitoring period. For example, individual health risk indicators could be provided for metabolic syndrome, atherosclerosis, hypertension, high blood glucose, unfavourable blood lipid profile, obesity etc. Alternatively, a percentage general risk factor for developing lifestyle-related diseases could be provided, or one or more percentage risk factors for developing specific lifestyle-related diseases. A binary indication could be provided whether or not the user has been active enough over the monitoring period to increase their life expectancy, or a life expectancy could be provided. The provision of these indicators comprises comparison with population study data, and the provision of some comprise taking into account additional data relating to the user such as age, weight, body mass index, smoking and alcohol drinking habits and diet and/or monitoring of other biometric parameters.

At step 440, the health risk indicator is provided to the user or a medical professional, for example via a user interface, at the end of a first monitoring period. For example a report, or an alert that a report can be accessed by, for example, selecting a hyperlink or opening an application, could be text messaged or emailed to an account of the user or medical professional, or an application running in the background of a user device could automatically open or trigger an alert. Alternatively, the user or medical professional could be required to manually request a report when desired. The system's software could provide the user with an opportunity to share each or every report on linked social media accounts.

Figure 5:
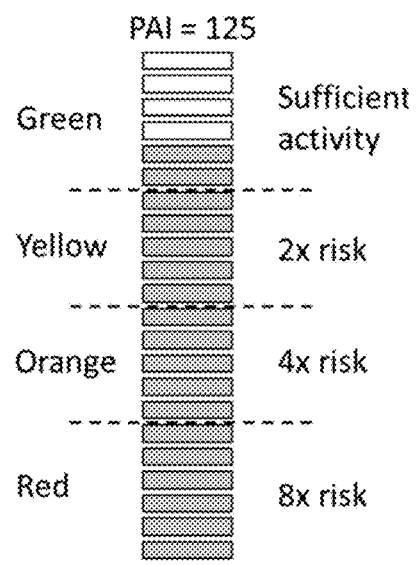
FIG. 5 shows an example user interface.
Figure 6A:
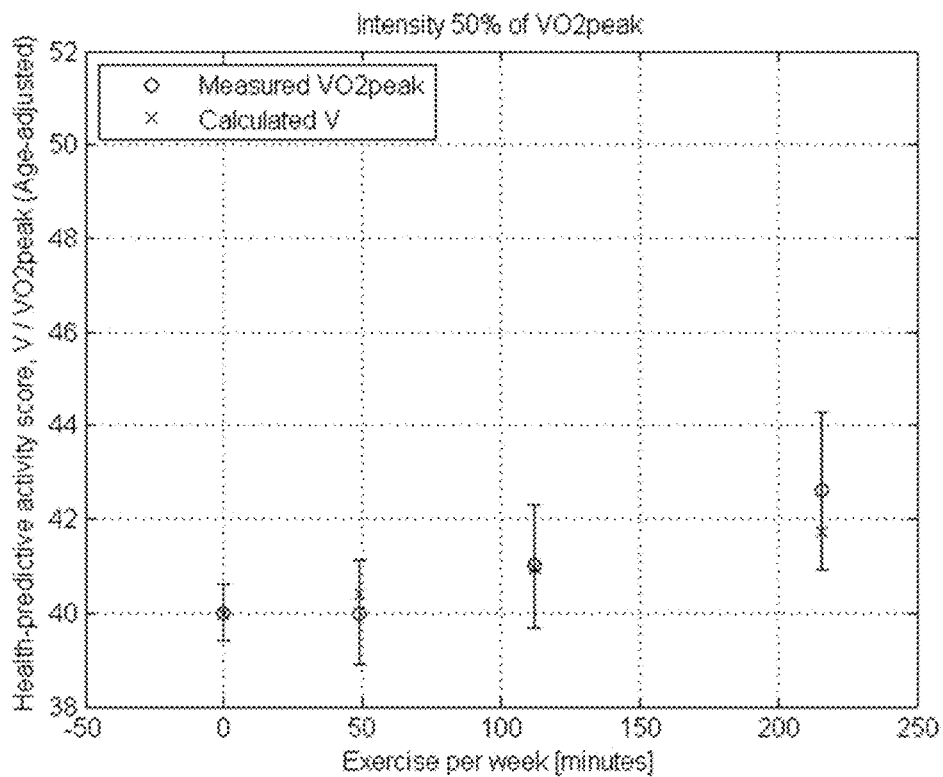
FIGS. 6a to 6d illustrate example data.
Figure 6B:
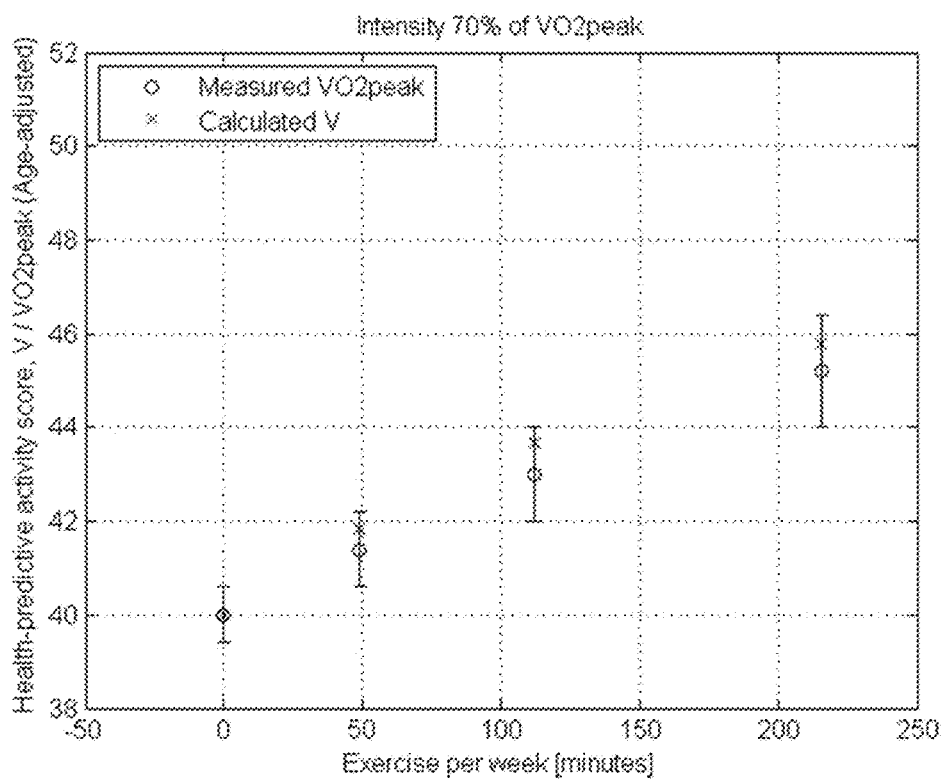
Figure 6C:
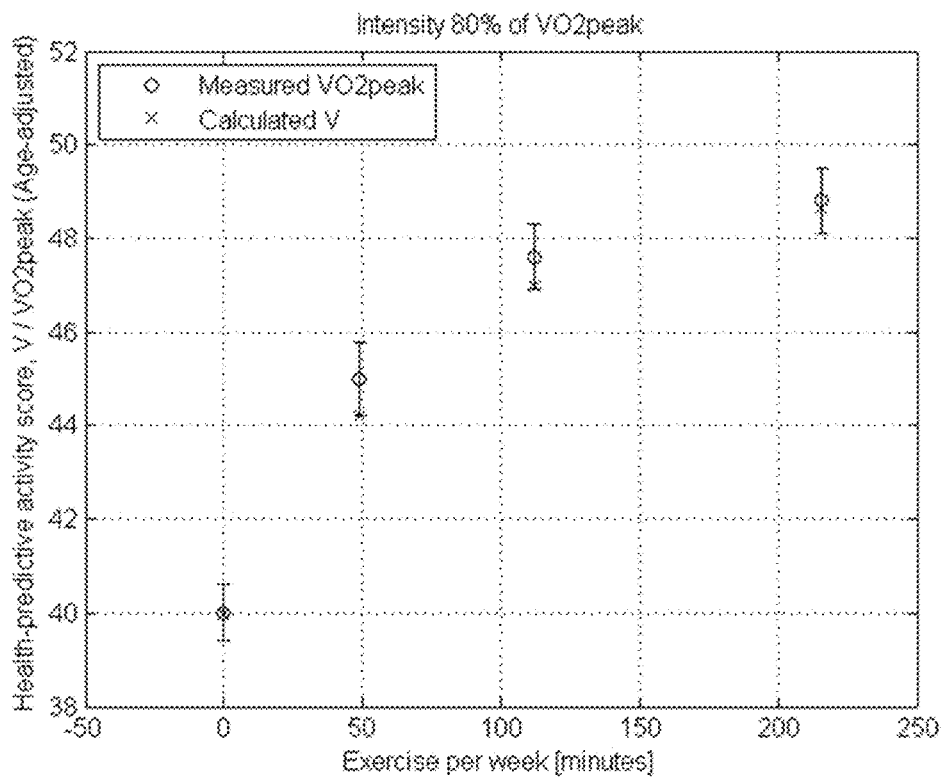
Figure 6D:
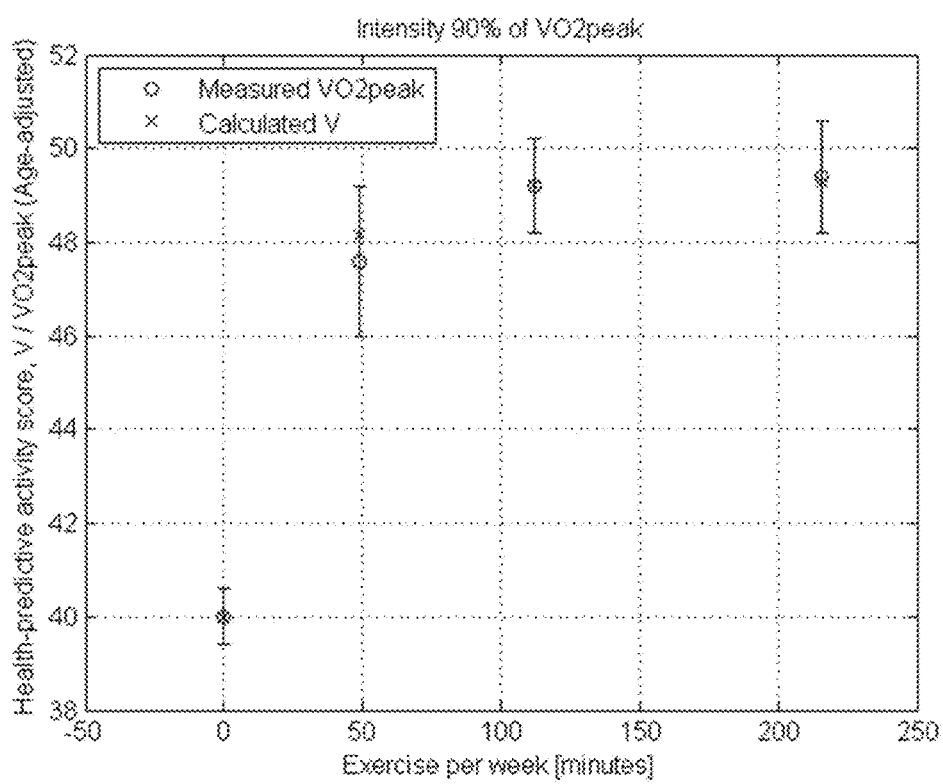

A graphical user interface displaying a health risk indicator could for example be as shown in FIG. 5. The PAI is indicated at the top and graphically represented below by coloured bars indicating risk of developing lifestyle-related diseases. In the example shown, the PAI is 125, above the threshold for sufficient activity for minimal risk (100), so the coloured bars fill up to the green zone above the upper divider line.

A second monitoring period could follow consecutively from the first such that up to date health risk indicators are available at a frequency of one divided by the monitoring period, for example once per week. Alternatively, the monitoring period could be a sliding window so that, for example, up to date health risk indicators are available daily based on data collected over the preceding 7 days.

Health benefit from activity diminishes as activity level increases, the most benefit being shown from an increase from complete inactivity to only a little activity. Accordingly, the aggregate heartbeat value could be calculated by use of a function that lowers the weighting of higher activity scores.

If user motion data is obtained for some or all of the monitoring period, for example if sensor device 210 or an additional sensor device comprises a motion sensor such as a tri-axis accelerometer, this can be taken into account in determination of the health risk indicator. For example if a user's heart rate is high (with respect to their resting and maximum heart rate) but they do not appear to be moving, this could be due to emotional stress rather than physical exertion. Therefore the high weighting which would be given to the heartbeats in that high heart rate period according to the method above could provide a false indication of activity level. The weighting applied could therefore be reduced, for example by 15%, for periods during which the measured (or extrapolated) heart rate is higher than would be expected for the activity level suggested by the motion sensor, for example by a predetermined margin such as 30 beats per minute.

A relatively high measured heart rate (with respect to the user's resting and maximum heart rates) during a period in which a motion sensor suggests the user is not moving could be an indication of heart disease, especially if sustained over hours (Nauman et al, JAMA 2011). If this condition is determined to be sustained over a predetermined period of, for example, two hours the system could inform the user to contact his/her physician for a medical follow-up.

If such a combined pulse and motion sensor approach is used then greater accuracy could be obtained if, during exercise, the user ensures they wear the motion sensor on an active part of their body. For example, a wrist-worn motion sensor could result in inappropriate decreased weighting of heart rate data collected during cycling, whereas an ankle-worn motion sensor would not. The system could alert the user via a user interface if heart rate data and motion sensor data do not indicate similar activity levels, for example if measured (or extrapolated) heart rate is higher than would be expected for the activity level suggested by the motion sensor by said predetermined margin. Such an indication could, for example encourage the user to switch the motion sensor to a more appropriate part of their body during exercise (e.g. transfer a band-based motion sensor from wrist to ankle for cycling), or could indicate to heart patients that they are under undesirable emotional stress and should rest if possible.

A further parameter that can be determined from the heart rate data is the user's peak aerobic capacity, or peakVO$_2$. An aggregate heartbeat value, for example the health-predictive activity score, V, can be statistically fitted to data that includes peakVO$_2$. However, since the present invention provides an instantaneous assessment of current activity level (typically over a one-week-period) it cannot explicitly determine peakVO$_2$. peakVO$_2$ evolves over time, increasing slowly with an elevated physical activity profile and decreasing slowly with absence of (or lowered) physical activity. However, persistence of a certain activity score V will converge towards a peakVO$_2$ value determined from the data fitting of V the model. An activity-induced peakVO$_2$ estimate, AIpeakVO2$_k$, could be estimated by a low pass filter on V, for example a first order low pass filter as per equation 7:

$$AIpeakVO2_k = \alpha V_k + (1-\alpha) AIpeakVO2_{k-1} \quad (7)$$

where α is a constant given by the time constant expressing the individual's response to training α can be an average value determined from a population study and/or individually fitted by analysing the slowly-varying changes in resting heart rate of the user. The activity-induced peakVO$_2$ estimate could be further corrected to a true peakVO$_2$ estimate by using the user's age, resting heart rate and/or waistline measurement/body mass index (Nes et al 2011 & Nes et al, unpublished data).

FIGS. 6*a* to 6*d* show how health-predictive activity score, V, as calculated according to equation 5 relates to peakVO$_2$ for test subjects respectively performing various amounts of exercise per week at 50, 70, 80 and 90% of peak oxygen uptake.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications can be made within the scope of the invention.

What is claimed is:

1. A wearable heart rate monitor for determining health risk comprising:
   a sensor configured to obtain heart rate data for a user over a monitoring period;
   a processor; and
   a memory, wherein instructions stored in the memory, when executed by the processor, direct the processor to:
      obtain motion information indicative of motion of the user;
      derive an aggregate heartbeat value for the user over said monitoring period based, at least in part, on biometric data for the user,
         wherein the aggregate heartbeat value is derived by weighting heart rate values by:
            in a first case where the motion information indicates movement by the user and respective heart beat values are higher than an expected heart rate level, based on the motion information, by at least a first predetermined margin, or in a second case where the motion information indicates no movement by the user and the respective heart beat values are lower than the expected heart rate level by at least the first predetermined margin, weighting the heart rate values such that the weighting is proportional to the heart rate values; and
            in a third case where the motion information indicates movement by the user but the respective heart beat values are lower than the expected heart rate level by at least the first predetermined margin, or in a fourth case where the motion information indicates no movement by the user but the respective heart beat values are higher than the expected heart rate level by at least the first predetermined margin, assigning reduced weights to the heart rate values; and
wherein the heart rate values are obtained according to a variable sampling rate that is selected based on a comparison of at least one previous heart beat measurement to
a heart rate range that is a difference between a maximum heart rate of the user and a resting heart rate of the user;
determine a health-predictive activity score based on the aggregate heartbeat value for the user; and
determine a health risk indicator from the health-predictive activity score according to a model associating, for a plurality of subjects, a respective activity score to a respective peak oxygen uptake, the model used to compare the health-predictive activity score with an activity score needed to achieve a certain peak oxygen uptake over time to determine the health risk indicator.

2. The wearable heart rate monitor of claim 1, wherein the sensor senses the user's pulse over the monitoring period to produce a series of pulse measurements for the heart rate data, and wherein the instructions direct the processor to determine the aggregate heartbeat value using the series of pulse measurements.

3. The wearable heart rate monitor of claim 2, further comprising interpolating said series of pulse measurements to produce an evenly distributed series of data points or a continuous heart rate function over the monitoring period.

4. The wearable heart rate monitor of claim 1, wherein the instructions that direct the processor to process said heart rate data comprise instructions to normalise the heart rate data, an evenly distributed series of data points derived from the heart rate data or a continuous function derived from the heart rate data by subtracting a resting heart rate value of the user from a measured heart rate value of the user and dividing a result by the difference between the maximum heart rate of the user and the resting heart rate of the user.

5. The wearable heart rate monitor of claim 1, further comprising a user interface, wherein the instructions further direct the processor to provide the health risk indicator to the user through the user interface.

6. A system for enhancing health monitoring technology comprising computer-executable instructions for performing a method comprising:
obtaining heart rate data, from a wearable device, for a user recorded over a monitoring period by steps comprising:
calculating a heart rate range as a difference between a maximum heart rate of the user and a resting heart rate of the user;
for the monitoring period, repeatedly
measuring a current heart rate value according to a variable sampling rate that is selected based on a comparison of a previous heart rate measurement to the heart rate range;
obtaining, from the wearable device, motion information indicative of motion of the user;
determining, using the motion information, an activity level;
in a case that the heart rate data is higher than expected heart rate data for the activity level, alerting the user to place the wearable device on a different body part;
processing said heart rate data based, at least in part, on biometric data for the user to determine an aggregate heartbeat value for the user over said monitoring period by steps comprising:
determining a series of intensity scores $z_k$ or an intensity score function $z(t)$ from a series of normalized heart rate values $\bar{y}_k$ or a continuous normalised heart rate function $\bar{y}(t)$) obtained from the heart rate data based, a constant scaling factor $c_1$, and a constant weighting factor $c_2$ according to: $z_k = c_1(e^{c_2\bar{y}_k}-1)$ or $z(t)=c_1(e^{c_2\bar{y}_k}-1)$, wherein $c_1$ and $c_2$ are chosen from a plurality of options according to one or more user characteristics;
determining a health-predictive activity score based on the aggregate heartbeat value of the user; and
determining a health risk indicator from the health-predictive activity score according to a model associating, for a plurality of subjects, a respective activity score to a respective peak oxygen uptake, the model used to compare the health-predictive activity score with an activity score needed to achieve a certain peak oxygen uptake over time to determine the health risk indicator.

7. A method of determining a health risk indicator for a user by:
obtaining heart rate data for the user recorded over a monitoring period by steps comprising:
sensing the user's pulse over the monitoring period to produce a series of pulse measurements, wherein the heart rate data comprising the series of pulse measurements, the sensing comprising:
calculating a heart rate range as a difference between a maximum heart rate of the user and a resting heart rate of the user;
for the monitoring period,
measuring a current heart rate value according to a variable sampling rate that is selected based on a comparison of a previous heart rate measurement and the heart rate range;
obtaining motion information indicative of motion of the user over the monitoring period;
processing said heart rate data based, at least in part, on biometric data for the user to determine an aggregate heartbeat value for the user over said monitoring period, wherein
the aggregate heartbeat value is derived by weighting heart rate values by:
determine an expected heart rate level based on the motion information;
in a first case where the motion information indicates movement by the user but respective heart beat values are lower than the expected heart rate level by at least a first predetermined margin, or in a second case where the motion information indicates no movement by the user but the respective heart beat values are higher than the expected heart rate level by at least a second predetermined margin, assigning reduced weights to the heart rate values;
determining a health-predictive activity score based on the aggregate heartbeat value for the user; and
determining said health risk indicator from the health-predictive activity score according to a model associating, for a plurality of subjects, a respective activity score to a respective peak oxygen uptake, the model used to compare the health-predictive activity score with an activity score needed to achieve a certain peak oxygen uptake over time to determine the health risk indicator.

8. The method of claim 7, wherein said biometric data comprises a resting heart rate value for the user and a maximum heart rate value for the user.

9. The method of claim 8, wherein said processing said heart rate data comprises normalising the heart rate data, an evenly distributed series of data points derived from the heart rate data or a continuous function derived from the heart rate data by subtracting the resting heart rate value from a measured heart rate value and dividing a result by the difference between the maximum heart rate and the resting heart rate.

10. The method of claim 7, further comprising providing the health risk indicator to the user.

11. The method of claim 7, wherein the monitoring period is at least five days.

12. The method of claim 7, wherein the aggregate heartbeat value is determined using said series of pulse measurements.

13. The method of claim 12, further comprising interpolating said series of pulse measurements to produce an evenly distributed series of data points or a continuous heart rate function over the monitoring period.

14. The method of claim 7, wherein processing the said heart rate data further comprising:
in a third case where the motion information indicates movement by the user and the respective heart beat values are higher than the expected heart rate level by at least a third predetermined margin, or in a fourth case where the motion information indicates no movement by the user and the respective heart beat values are lower than the expected heart rate level by at least a fourth predetermined margin, weighting the heart rate values such that the higher the heart rate value, the more weight it is given.

15. The method of claim 7, wherein the health risk indicator is determined by statistical fitting of the aggregate heartbeat value with population survey data.

16. The method of claim 7, repeated periodically, with a repetition period:
equal to the monitoring period such that the method is repeated consecutively; or
equal to the monitoring period such that the method is repeated over a sliding window.

17. The method of claim 7, further comprising estimating the user's peak aerobic capacity using a low pass filter on the aggregate heartbeat value or a value derived therefrom and the biometric data for the user.

* * * * *